(12) United States Patent
Moczygemba

(10) Patent No.: US 11,974,942 B2
(45) Date of Patent: May 7, 2024

(54) THERMOELECTRIC CONTRAST THERAPY DEVICE

(71) Applicant: II-VI Delaware, Inc, Wilmington, DE (US)

(72) Inventor: Joshua Edward Moczygemba, Winona, TX (US)

(73) Assignee: II-VI DELAWARE, INC., Wilmington, DE (US)

(*) Notice: Subject to any disclaimer, the term of this patent is extended or adjusted under 35 U.S.C. 154(b) by 691 days.

(21) Appl. No.: 15/734,975

(22) PCT Filed: Jun. 19, 2019

(86) PCT No.: PCT/US2019/038050
§ 371 (c)(1),
(2) Date: Dec. 3, 2020

(87) PCT Pub. No.: WO2019/246306
PCT Pub. Date: Dec. 26, 2019

(65) Prior Publication Data
US 2021/0228405 A1    Jul. 29, 2021

Related U.S. Application Data

(60) Provisional application No. 62/687,145, filed on Jun. 19, 2018.

(51) Int. Cl.
*A61F 7/02* (2006.01)
*A61F 7/00* (2006.01)

(52) U.S. Cl.
CPC ............. *A61F 7/007* (2013.01); *A61F 7/02* (2013.01); *A61F 2007/0075* (2013.01);
(Continued)

(58) Field of Classification Search
CPC ...... A61F 2007/0075; A61F 2007/0077; A61F 2007/0093; A61F 2007/0292; A61F 7/007; A61F 7/02
See application file for complete search history.

(56) References Cited

U.S. PATENT DOCUMENTS

| | | | |
|---|---|---|---|
| 8,397,518 B1* | 3/2013 | Vistakula | A61F 7/02 62/3.5 |
| 2006/0235498 A1* | 10/2006 | Mollendorf | A61F 7/02 607/104 |

(Continued)

FOREIGN PATENT DOCUMENTS

WO    2006/086618 A1    8/2006

OTHER PUBLICATIONS

International Search Report and Written Opinion issued in PCT/US2019/038050, dated Oct. 7, 2019.

*Primary Examiner* — Michael F Peffley
(74) *Attorney, Agent, or Firm* — Blank Rome LLP

(57) ABSTRACT

This disclosure provides an apparatus for a thermoelectric (TE) contrast therapy device and related methods. The thermoelectric contrast therapy device includes a control node (610) and a plurality of thermoelectric nodes (605). The control node electrically and mechanically connected to the plurality of thermoelectric nodes, the control node configured to direct the heating and cooling functions as well as timing functions. Each of thermoelectric nodes includes a thermoelectric module (105) structured with a supply side (115) and a waste side (120), a phase change material (110), a reservoir (725), a thermal sink (320), a spreader (125) and a controller (1010). The thermoelectric contrast therapy device pre-charges (1105) the PCM contained in the reservoir; provides (910) opposite heating and cooling functions using the supply side and the waste side of the thermoelec- (Continued)

tric module; and directs, using the controller, the heating and cooling functions as well as timing functions.

15 Claims, 11 Drawing Sheets

(52) U.S. Cl.
    CPC ............... *A61F 2007/0077* (2013.01); *A61F 2007/0093* (2013.01); *A61F 2007/0292* (2013.01)

(56) References Cited

U.S. PATENT DOCUMENTS

| | | | |
|---|---|---|---|
| 2007/0193278 A1* | 8/2007 | Polacek | F25B 21/02 62/3.2 |
| 2014/0352325 A1* | 12/2014 | Brown | A61B 18/02 62/3.2 |
| 2017/0027053 A1* | 1/2017 | Moczygemba | H05K 1/0203 |
| 2018/0289531 A1* | 10/2018 | Thomas | A61F 7/007 |
| 2018/0347869 A1* | 12/2018 | Boule | F25B 21/02 |

* cited by examiner

THERMOELECTRIC CONTRAST THERAPY DEVICE

TECHNICAL FIELD

The present application relates generally to contrast therapy and, more specifically, to a thermoelectric device for performing contrast therapy.

BACKGROUND

Contrast bath therapy, also known as "hot/cold immersion therapy," is a form of treatment where a limb or the entire body is immersed in warm water followed by the immediate immersion of the limb or body in ice water. This procedure is repeated several times, alternating hot and cold. Note that the treatment is recommended to end in the ice water, as heat will induce the body's inflammatory response, while cold helps to decrease inflammation.

SUMMARY

This disclosure provides a thermoelectric contrast therapy device.

In a first embodiment, a thermoelectric contrast therapy device is provided. The thermoelectric contrast therapy device includes a thermoelectric module, a phase change material (PCM), a reservoir, a thermal sink, a spreader, and a controller. The thermoelectric module is structured with a supply side and a waste side, wherein the supply side and the waste side provide opposite heating and cooling functions based on a polarity of an input voltage applied to the thermoelectric module. The phase change material (PCM) is positioned on the waste side of the thermoelectric module, wherein the PCM is capable of being pre-cooled before operation of the thermoelectric module. The reservoir contains the PCM. The thermal sink contacts the PCM and the thermoelectric module. The spreader is positioned on the supply side of the thermoelectric module. The controller directs the heating and cooling functions as well as timing functions.

In certain embodiments, the thermal sink extends into the PCM for enhanced heat transfer. The reservoir can be detachably coupled for separate charging. The spreader is flexible or structured with a contour. The spreader and the thermal sink can include a corrosion protective coating. The thermoelectric module can be electrically isolated from the thermal sink and the spreader. The reservoir can include a cap that can drain and refill the PCM inside the reservoir. The controller can monitor the supply temperature sensor and the waste temperature sensor based on pre-programmed safety features that prevent user abuse.

In certain embodiments, the thermoelectric contrast therapy device can further include a supply temperature sensor located on the supply side of the thermoelectric module; and a waste temperature sensor located on the waste side of the thermoelectric module. The thermoelectric contrast therapy device can also include structural foam provided between the thermal sink and the spreader and configured to mechanically couple and thermally isolated the thermal sink and the spreader.

In a second embodiment, a thermoelectric contrast therapy device with a plurality of thermoelectric nodes and a control node is provided. Each thermoelectric node includes a thermoelectric module, a phase change material (PCM), a reservoir, a thermal sink, and a spreader. The thermoelectric module is structured with a supply side and a waste side, wherein the supply side and the waste side provide opposite heating and cooling functions based on a polarity of an input voltage applied to the thermoelectric module. The phase change material (PCM) is positioned on the waste side of the thermoelectric module, wherein the PCM is capable of being pre-cooled before operation of the thermoelectric module. The reservoir contains the PCM. The thermal sink contacts the PCM and the thermoelectric module. The spreader is positioned on the supply side of the thermoelectric module. The controller directs the heating and cooling functions as well as timing functions. The control node is electrically and mechanically connected to each of the thermoelectric nodes. The control node directs the heating and cooling functions as well as timing functions.

In certain embodiments, each of the thermoelectric nodes further comprises a PCM reservoir to contain the PCM. The control node can provide different amounts of the input voltage and the polarity of the input voltage to individual thermoelectric nodes.

In certain embodiments, the thermoelectric contrast therapy device can include a PCM reservoir to contain the PCM for each of the thermoelectric nodes. The thermoelectric contrast therapy device can also include an external PCM reservoir containing the PCM; a PCM loop connecting the external PCM reservoir to each of the thermal sinks; and a pump configured to circulate the PCM through the PCM loop. The thermoelectric device can include connections to attach at least one of the thermoelectric nodes to at least one thermoelectric nodes of a second thermoelectric contrast therapy device.

In a third embodiment, a method for applying contrast therapy to a body using a thermoelectric contrast therapy device is provided. The method includes pre-charging a PCM stored in a PCM reservoir, wherein the PCM is located on a waste side of a thermoelectric module. The method also includes receiving operational set points for an operation of a supply side of the thermoelectric module, wherein the operational set points include hot parameters, cold parameters and timing parameters. The method also includes controlling an application of an input voltage or current applied to a thermoelectric device based on the received operational set points, wherein the application includes an amount of the input voltage or current and a polarity of the input voltage.

In certain embodiments, the method can further include inserting the thermoelectric contrast therapy device in a strap designed for a specific body part; and attaching the strap to the specific body part. The method can further include controlling the thermoelectric module using an external device; and uploading usage history data of the application of the input voltage to the thermoelectric device.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 11, discussed below, and the various embodiments used to describe the principles of the present disclosure in this patent document are by way of illustration only and should not be construed in any way to limit the scope of the disclosure.

Implementation of contrast therapy treatment in a home type setting typically involves preparing an ice bath and a hot bath and then submerging the body part in them. Depending on the part of the body requiring treatment, this may or may not be practical. Another option is physically switching hot and cold "gel" packs on the affected body part. Again, labor intensive and tedious. Clinical type machines are on the market, but these powered contrast therapy systems are typically comprised of hot and cold fluid loops attached to a rather large heater/chiller unit in clinical type setting. Again, not readily available to everyday users. The novelty of this approach is a fast transient, direct conduction, low cost, and flexible programmable contrast therapy device that eliminates the undesirable setup and application of traditional contrast therapy options. The system can be wall powered or battery powered options to provide for mobility. The discreet thermoelectric/phase change material (PCM) nodes provide flexibility and conformability with the body.

A contrast therapy device that is thermoelectric based is provided. The thermoelectric contrast therapy device functions by using a pre-charge (frozen) phase change material as the heat sink and relies on direct conduction of heat into and out of the skin from the thermoelectric device. The thermoelectric contrast therapy device takes advantage of the alternating hot and cold cycles to extend a PCM charge (TE pulls heat from the PCM during the skin heating phase). The thermoelectric contrast therapy device allows for typical contrast therapy cycle temperatures of 10° C. to 45° C., and programmable to custom settings as well via wired or blue-tooth capability. The thermoelectric device can be linked to wireless device applications. The thermoelectric device can be either wall or battery powered. The thermoelectric device is designed to be flexible to conform to various body parts by using discreet thermoelectric module/couples and discreet PCM cavities. Also can be strapped on to body as well.

Figure 1:
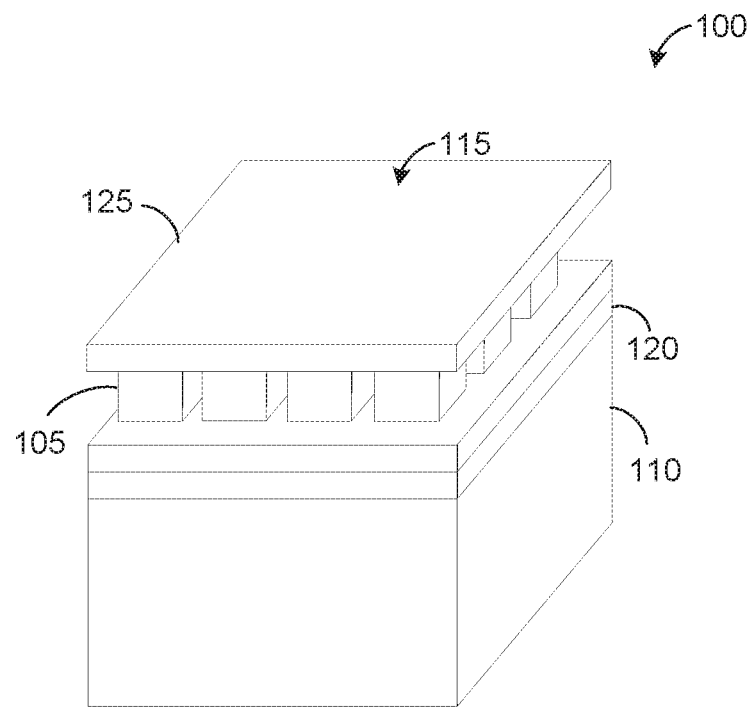
FIG. 1 illustrates an example thermoelectric contrast therapy assembly according to this disclosure.

FIG. 1 illustrates an example thermoelectric contrast therapy device 100 according to this disclosure. The embodiment shown in FIG. 1 is for illustration only. Other embodiments could be used without departing from the scope of the present disclosure.

The thermoelectric contrast therapy device 100 can provide heating and cooling to a user. The thermoelectric contrast therapy assembly includes a thermoelectric module 105 and a phase change material (PCM) 110.

The thermoelectric module 105 is a solid state heat pump that pumps heat from a cold side to a hot side. The thermoelectric module 105 includes a supply side 115 and a waste side 120. When electricity is provided to the thermoelectric module 105, the supply side 115 and waste side 120 provide an opposite effect of either heating or cooling. That is, when the electrical energy is provided in a first direction, the supply side 115 experiences a heating effect and the waste side 120 experiences a cooling effect. When the electrical energy is provided in a second direction, that is opposite of the first direction, the supply side 115 experiences a cooling effect and the waste side 120 experiences a heating effect.

The supply side 115 can be applied directly to a surface (e.g., human skin) used for contrast therapy. Typically, the contrast therapy could use a 1:1-4 heat-to-cool ratio for a contrast therapy cycle. The supply side 115 includes a spreader 125 for distributing the heat exchange across the surface of the supply side 115 of the thermoelectric module 105. Secondary spreaders located within the spreaders of the supply side 115 of the thermoelectric module 105 could also be included on the supply side 115, such as a piece of aluminum foil.

The PCM 110 is provided on the waste side 120 of the thermoelectric module 105. The PCM 110 can be pre-cooled or frozen to enhance the efficiency during the heating on the waste side 120 corresponding to the cooling effect provided on the supply side 115. When the supply side 115 is performing the heating effect, the waste side 120 is providing cooling to the PCM 110 or "recharging" the PCM 110 in a reverse melting process. A heat spreader can be implemented within the PCM 110. An example of a PCM 110 that could be implemented with the thermoelectric contrast therapy device 100 is water. The thermoelectric contrast therapy device 100 could be stored in a freezer before a therapy session to charge the PCM 110 for extended use of the thermoelectric contrast therapy device 100.

Figure 2:
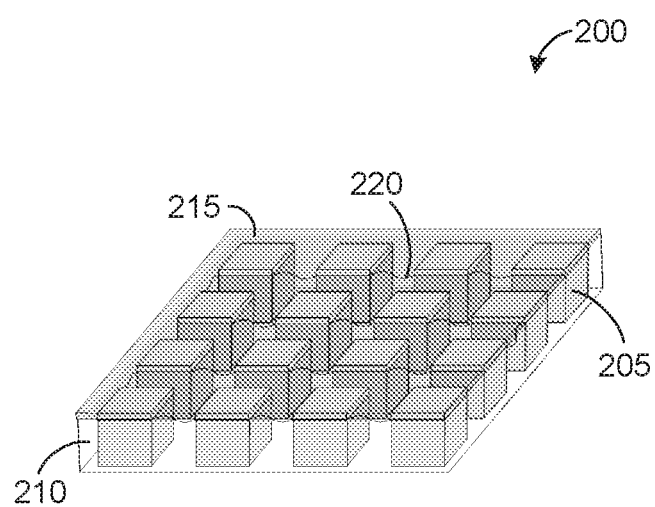
FIG. 2 illustrates an example discreet thermoelectric assemblies array according to various embodiments of the present disclosure.

FIG. 2 illustrates an example discreet thermoelectric assemblies array 200 according to various embodiments of the present disclosure. The embodiment shown in FIG. 2 is for illustration only. Other embodiments could be used without departing from the scope of the present disclosure.

The discreet array 200 provides heating and cooling effects across a flexible surface. The discreet array 200 includes a plurality of thermoelectric contrast therapy assemblies 205, a flexible insulation layer 210 (such as foam, polymer, air, etc.), a cover fabric 215, and a plurality of electrical conductors 220. The array 200 allows for bending in multiple planes for accommodation of different body parts and shapes.

The plurality of thermoelectric assemblies 205 are spaced apart in the flexible insulation layer 210 and covered with the cover fabric 215. The array 200 provides enough flexibility for small or large body parts. The thermoelectric assemblies 205 could be the thermoelectric contrast therapy device 100 illustrated in FIG. 1 or the thermoelectric assembly 300 illustrated in FIG. 3. The thermoelectric assemblies 205 could be arranged in a grid, swirl or other patterns.

The insulation layer 210 insulates the PCM 110 in each thermoelectric assembly 205 from outside the array 200. The insulation layer 210 could be around each individual PCM 110 or around an aggregate of the thermoelectric assemblies 205 sharing a PCM 110 that traverses all of the thermoelectric assemblies 205. In addition, the array 200 could include a single PCM 110 that is shared as a common heat sink for every thermoelectric module in the array 200.

The spacing of the thermoelectric assemblies 205 allows the entire array 200 to be flexible while providing the heating and cooling evenly across the cover fabric 215. The spacing can be uniform or variable. For example, when the thermoelectric assemblies are implemented in a strap, the thermoelectric assemblies could be spaced with greater concentration in a center portion of the strap where the contact of the skin that is receiving the contrast therapy.

The thermoelectric assemblies 205 can be completely covered by the fabric 215, or the thermoelectric assemblies 205 can protrude through apertures in the fabric 215 for direct skin contact. These apertures could include "ring" type structures that allow the thermoelectric assembly 205 to snap into the fabric providing both a means for mechanical and electrical connections. Also, the fabric 215 could be fabric, foam sheet, plastic sheet, etc.

The plurality of the thermoelectric assemblies 205 are connected in a circuit using the electrical conductors 220 between each of the thermoelectric assemblies 205. The array 200 could include multiple circuits for controlling different temperature across the surface of the cover fabric 215. Multiple circuits of thermoelectric assemblies 205 could also provide increased versatility in controlling areas to receive the contrast therapy.

The electrical conductors 220 are used for both temperature sensing and power. The electrical conductors 220 can be flexible and stretchable. An example of an electrical conductor 220 is using conductive ink patterns printed on thermoplastic polyurethane (TPU). Another example is to use horseshoe shaped etched copper conductors on/embedded in TPU. Traditional wire or ribbon cable conductors can also be used. Contact between these electrical conductors 220 and the sensor and thermoelectric circuits could be made via conductive adhesives or films as well as traditional solders.

The cover fabric 215 covers the top of the thermoelectric assemblies 205. The cover fabric 215 is made of material that is flexible with the appropriate thermal and electrical properties.

Figure 3:
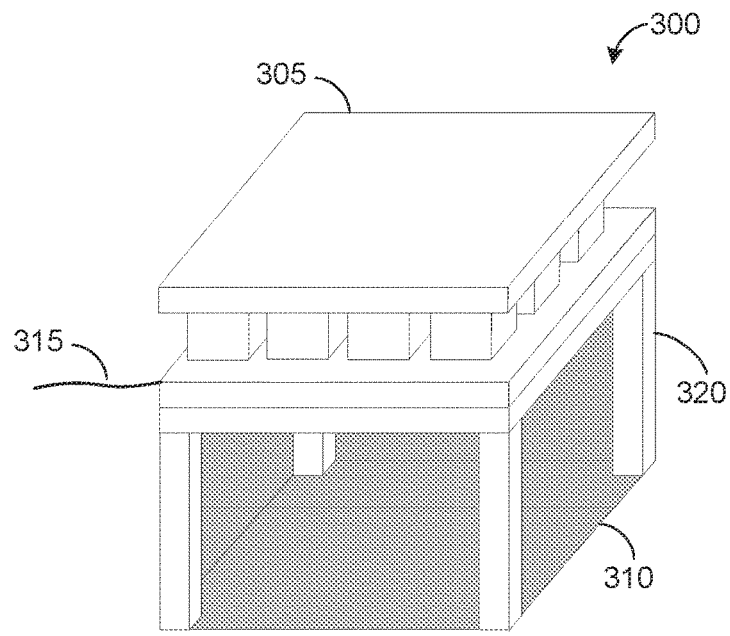
FIG. 3 illustrates a thermoelectric assembly with a heat spreader and phase change material vessel according to the embodiments of the present disclosure.

FIG. 3 illustrates a thermoelectric assembly 300 with a heat spreader/PCM vessel according to the embodiments of the present disclosure. The embodiment shown in FIG. 3 is for illustration only. Other embodiments could be used without departing from the scope of the present disclosure.

The thermoelectric assembly 300 is an example of one embodiment of the thermoelectric contrast therapy device 100. The thermoelectric assembly 300 includes a thermoelectric module 305, a PCM 310, a plurality of thermal sinks 320 or PCM vessels. The thermoelectric assembly 300 is connected to other thermoelectric assemblies 205 in the thermoelectric array 200 using electrical conductor 315.

In a thermoelectric contrast therapy device 100, as illustrated in FIG. 1, depending on polarity, the thermoelectric module either pumps heat from the supply side to the waste side, or pumps heat from the waste side to the supply side. Based on the direction of energy transfer, energy is either distributed into or pulled out of the PCM 110 through the thermal sinks 320. The thermal sink 320 enhances the efficiency of the thermal energy exchange between the PCM 110 and the waste side 120.

Adding thermal sinks 320 provides for a more even distribution of heat exchange between the waste side 120 and the PCM 310, increasing the efficiency of the thermoelectric module 305. The thermal sink can be any shape or size, but generally designed to distribute heat from the base of the thermal sink into the volume of the PCM.

Figure 4:
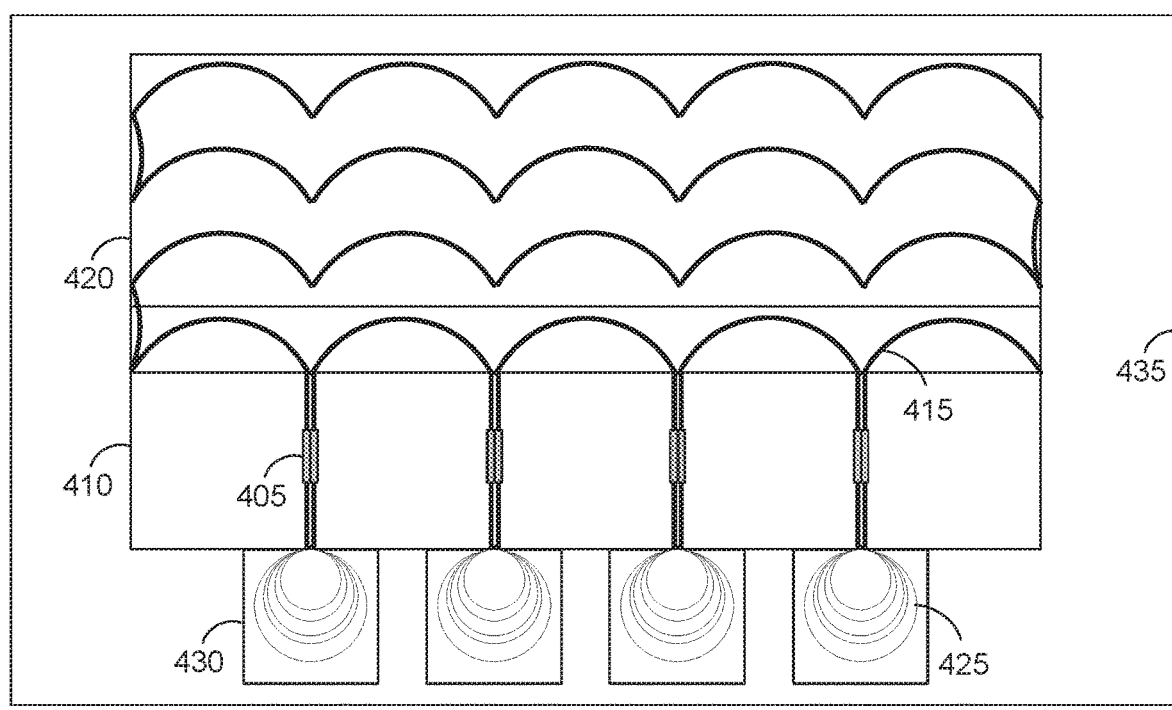
FIG. 4 illustrates a thermoelectric contrast therapy device with dispersed elements according to the embodiments of the present disclosure.

FIG. 4 illustrates a thermoelectric contrast therapy device 400 with dispersed elements according to the embodiments of the present disclosure. The embodiment shown in FIG. 4 is for illustration only. Other embodiments could be used without departing from the scope of the present disclosure.

The thermoelectric contrast therapy device 400 provides dispersed thermoelectric elements 405 in a flexible conductive spreader. The thermoelectric contrast therapy device 400 includes dispersed thermoelectric elements 405, a flexible insulator 410, flexible conductive wires 415, an insulating cover 420, a plurality of embedded thermal sink 425 and a discreet PCM 430. The thermoelectric contrast therapy device 400 is flexible enough to cover smaller and larger body parts.

The thermoelectric elements 405 are spaced apart throughout the flexible insulator 410. The thermoelectric elements 405 are spaced apart based on the shape of the thermoelectric contrast therapy device 400. The thermoelectric elements 405 can be entirely embedded within the flexible insulator 410.

The flexible insulator 410 is thick enough to keep the heat differential separate between the insulating cover 420 and the PCM 430. The flexible insulator 410 is made from a material that is both electrically and thermally isolating.

At least one flexible conductive wire 415 runs through the insulating cover 420. The flexible conductive wire 415 is connected to the supply side of each thermoelectric element 405 in series. The flexible conductive wire 415 exchanges the energy from the supply side of thermoelectric element throughout the flexible insulator 410. The flexible conductive wire 415 provides a spreading effect, similar to the spreader 125 illustrated in FIG. 1.

Each thermoelectric element 405 includes a thermal sink 425 connected to the waste side. The thermal sink 425 is embedded in the PCM 430 and causes thermal energy to be exchanged evenly throughout the PCM 430. A plurality of thermal sink 425 of different lengths or shapes can be attached to each PCM 430. The PCM 430 could be individual components for each of the thermoelectric elements 405 or a combined PCM 430 for all of the thermoelectric elements 405.

In certain embodiments, the thermoelectric device 400 can include or be inserted in a strap 435. The strap 435 can be attached to connections on the thermoelectric device 400. The insulating cover 420 could be implemented in the strap to extend the area of the contrast therapy. The strap 435 can be designed for specific body parts, such as wrist, elbow, knee, ankle, shoulder, etc.

Figure 5:
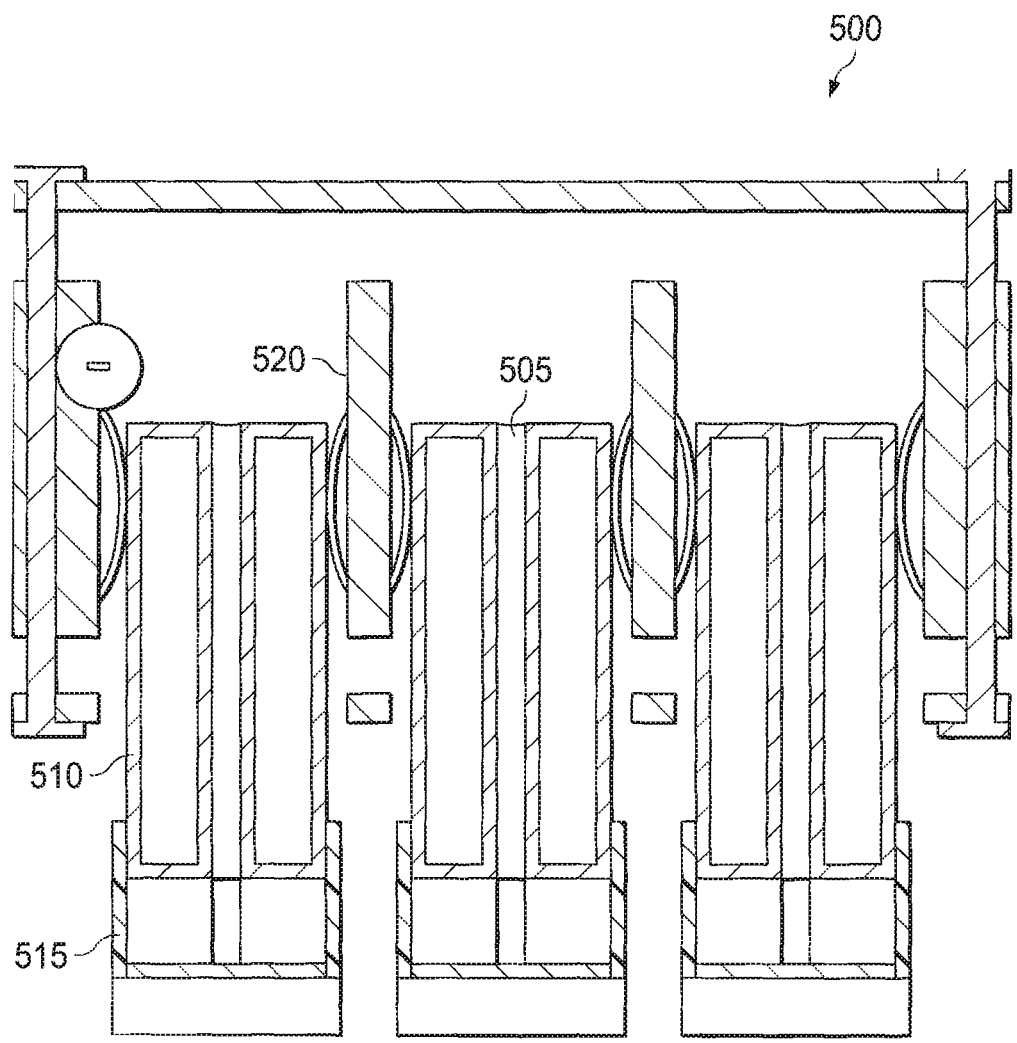
FIG. 5 illustrates a thermoelectric contrast therapy device with a plurality of thermoelectric impression probes according to the embodiments of the present disclosure.
Figure 6A:
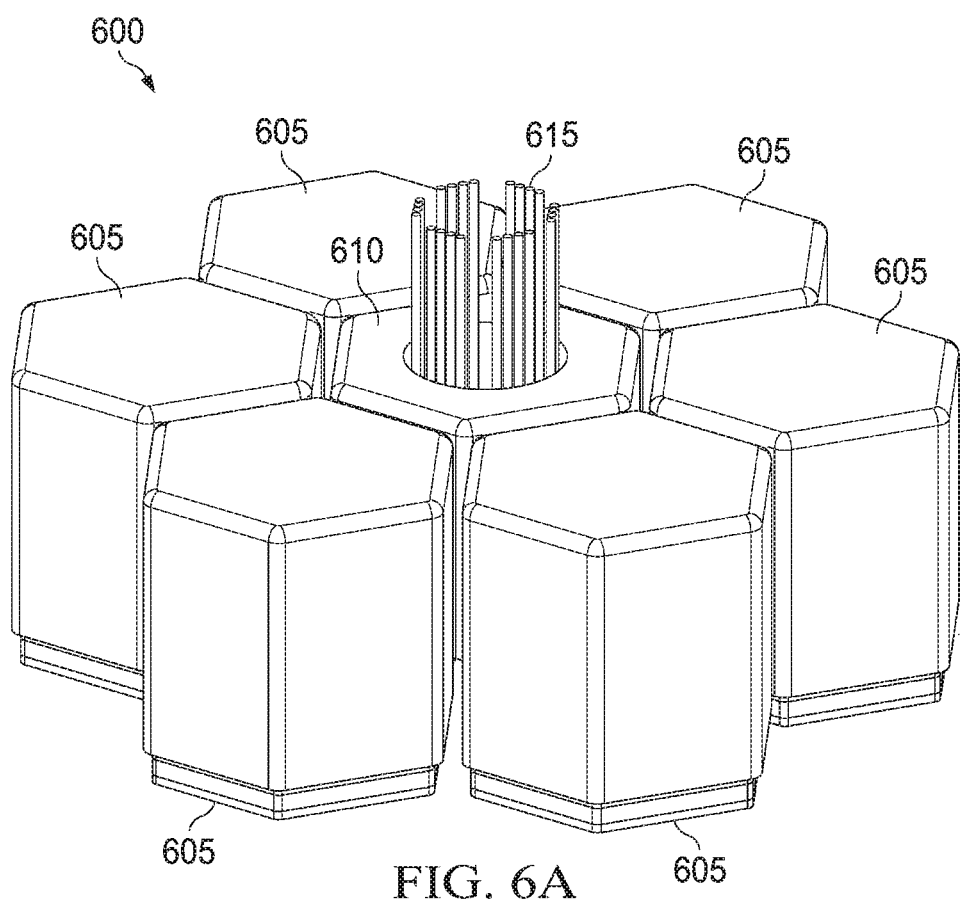
FIGS. 6A-6D illustrate an exemplary smart thermoelectric contrast therapy device according to the embodiments of the present disclosure.
Figure 6B:
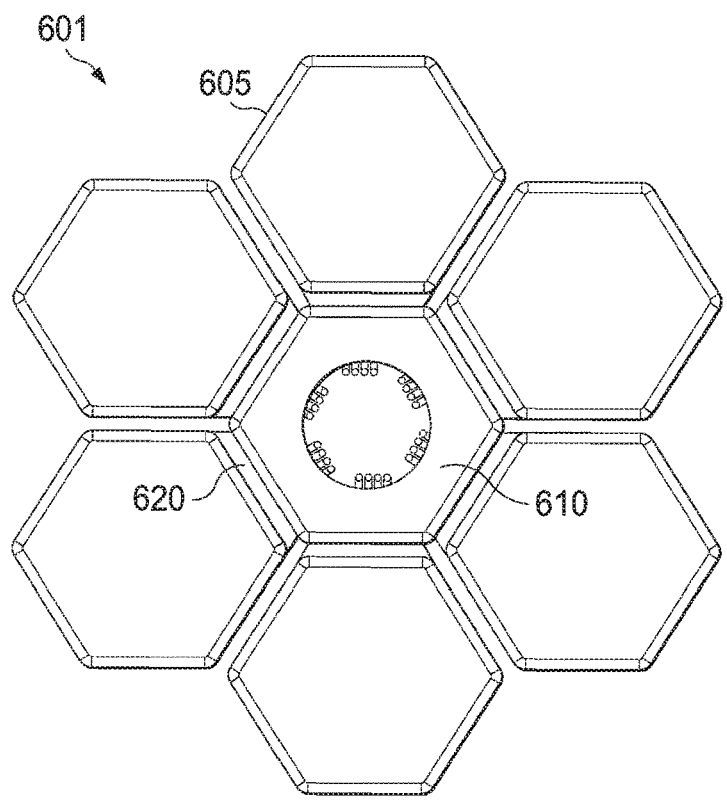
Figure 6C:
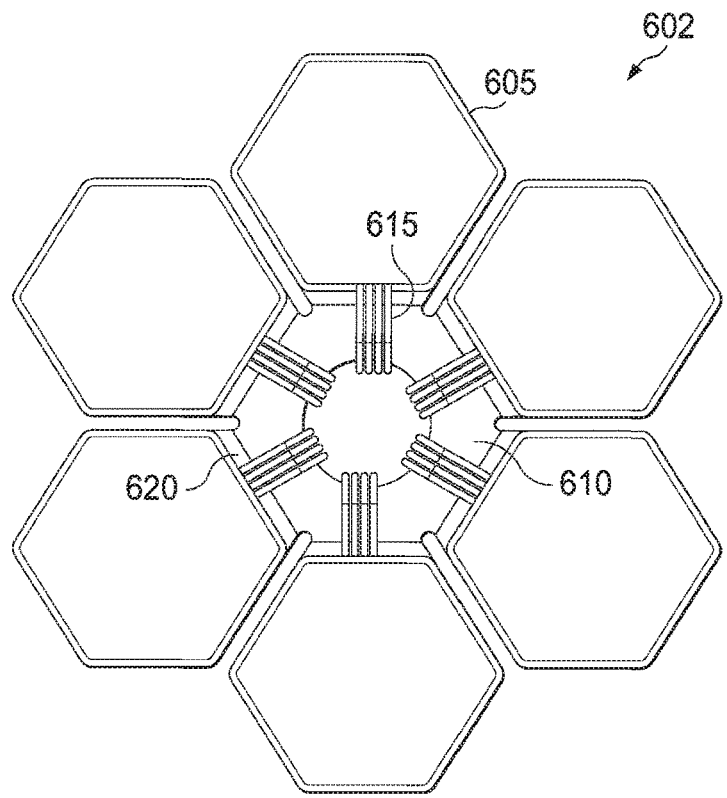
Figure 6D:
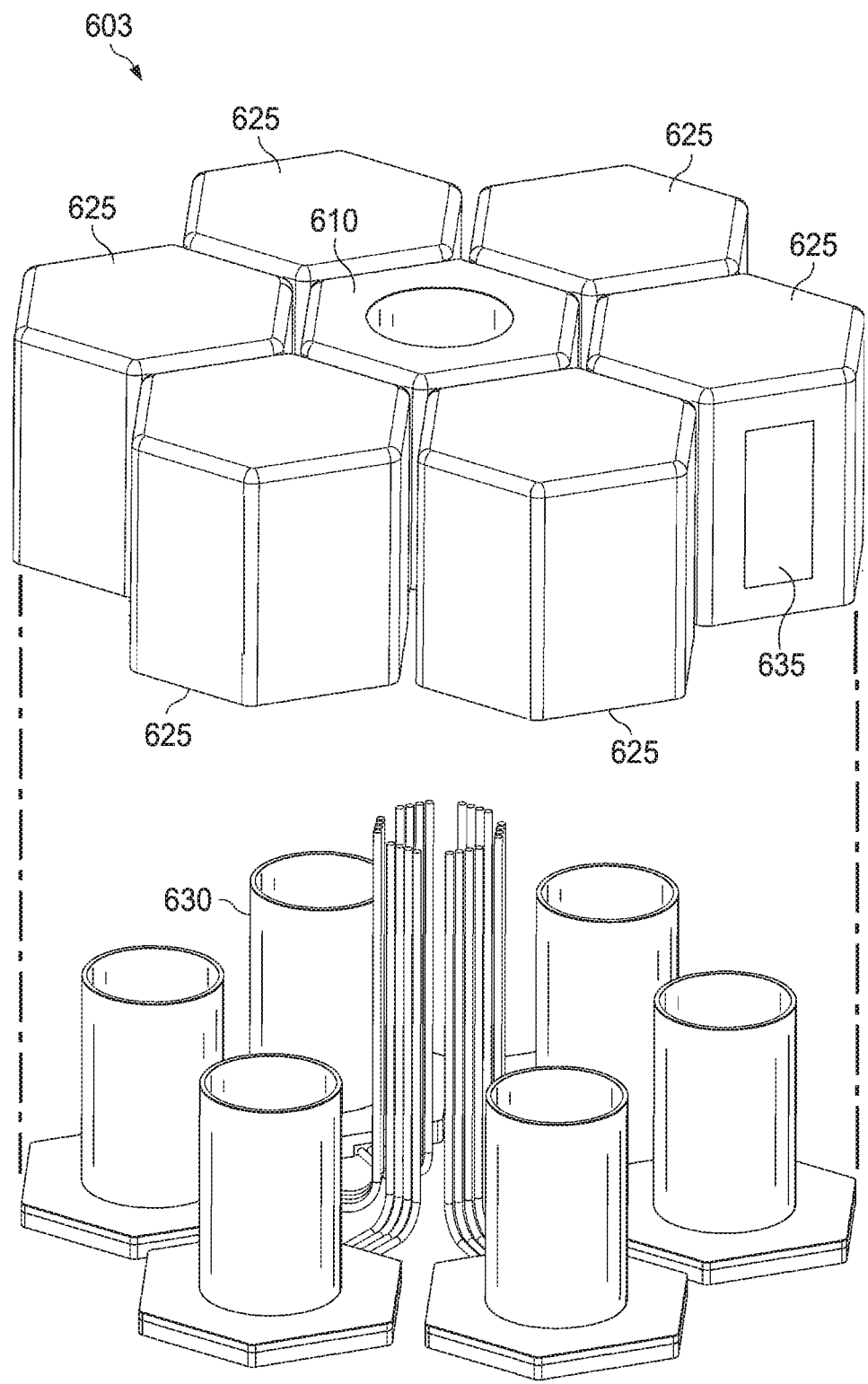

FIG. 5 illustrates a thermoelectric contrast therapy device 500 with a plurality of thermoelectric impression probes 505 according to the embodiments of the present disclosure. The embodiment shown in FIG. 5 is for illustration only. Other embodiments could be used without departing from the scope of the present disclosure.

The thermoelectric contrast therapy device 500 includes the thermoelectric elements in impression probes 505. Thermoelectric contrast therapy device 500 allows maximum conformation to various body parts. The thermoelectric contrast therapy device 500 does not require wiring, but is done with slip style connections and solder joints.

The impression probes 505 each include an electrically and thermally conductive tube 510 and insulator 515. The tube 510 serves as both a thermal conductor and an electrical conductor. The tube 510 contains the PCM and electrical connections. The insulator 515 is formed to add mechanical strength, thermal and electrical isolation as well as keep debris from entering the thermoelectric elements.

Each impression probe 505 is connected using breadboard style slip clip connections 520. This allows impression probes 505 to simultaneously transfer electricity during probe movement as the cumulative impression probes conform to the body part targeted by the contrast therapy. The movement of the probe 505 could also determine the amount of electrical energy provided to the thermoelectric element. This allows each thermoelectric element to operative independently of the other thermoelectric elements included in the thermoelectric contrast therapy device 500.

The design of the thermoelectric contrast therapy device 500 provides a possible Delta T control feedback via the Seebeck effect. The design of the thermoelectric contrast therapy device 500 also includes an electrically separated dual tube approach.

FIGS. 6A-6D illustrate an exemplary smart thermoelectric contrast therapy device 600 according to the embodiments of the present disclosure. The embodiments shown in FIGS. 6A-6D are for illustration only. Other embodiments could be used without departing from the scope of the present disclosure.

The smart thermoelectric contrast therapy device 600 includes a plurality of thermoelectric nodes 605 and a circuitry node 610. The plurality of thermoelectric nodes 605 and the circuitry node 610 can be structure in shapes with similar horizontal cross section based on the number of the plurality of thermoelectric nodes. As illustrated for a non-limiting example of the smart thermoelectric contrast therapy device 600, the assembly includes six thermoelectric nodes 605, each with a hexagonal cross section. Each of the thermoelectric nodes 605 has one side connected to a side of the circuitry node 610, which also is structured with a hexagonal cross section in the FIGS. 6A-6D. As the circuitry node 610 has a hexagonal cross section, the circuitry node 610 is connected to each of the thermoelectric nodes 605.

The circuitry node 610 includes a printed circuit board (PCB) and circuitry 615. The circuitry 615 connects to each of the thermoelectric nodes 605 and the PCB controls the direction of electricity for producing the heating and cooling operations. The PCB can also include any of the components of electronic device 1000. The PCB can be programmed with safety features such as time limits and temperature limits that prevent user abuse or user injury. The circuitry node 610 can include a power supply or be connected to a power supply. The power supply can be controlled by the circuitry node to provide power to the thermoelectric modules of each thermoelectric node.

The PCB and circuitry 615 can include a safety shut-off circuit that can disconnect specific thermoelectric nodes or all thermoelectric nodes. The shut-off circuit can be utilized in situations where the sensors reading show that a time limit or temperature limit has been exceeded. The shut-off circuit can also be used when a PCM reservoir has removed or is no longer charged.

The PCB and circuitry 615 can also include usage history storage circuitry. The usage history storage circuitry can store sensor readings and input settings. For example, the usage history storage circuitry can store the amount and polarity of the input voltage, the supply side temperature, the waste side temperature, the reservoir temperature, etc. The reservoir can include multiple temperature sensors to ensure consistent temperature throughout the PCM reservoir. The usage history storage circuitry can also include amounts of time for heating and cooling functions.

The node connections 620 between the circuitry node 610 and each of the thermoelectric nodes 605 can be made of a flexible material. For example, the flexible material can be a silicon based material. The flexible material of the node connections 620 allows for each individual thermoelectric node 605 to conform to rounded surfaces for greater surface area coverage.

Each thermoelectric node 605 includes a cover assembly 625 and a base assembly 630. The cover assembly 625 of the plurality of TECs can include mechanical or flexible exterior connections 635 for connecting multiple smart thermoelectric contrast therapy devices 600. The connections 635 can alternate on adjacent surfaces to have a male connection and a female connection, includes rails, slides, inserts, etc. The connections 635 can also include a female connection and male connections on opposite side of each exterior surface of the thermoelectric nodes 605, where the exterior surfaces are the surfaces not connected to the circuitry node 610 or adjacent to an adjacent thermoelectric node. The connections 635 can also be magnetically connected or snap connected.

Figure 7:
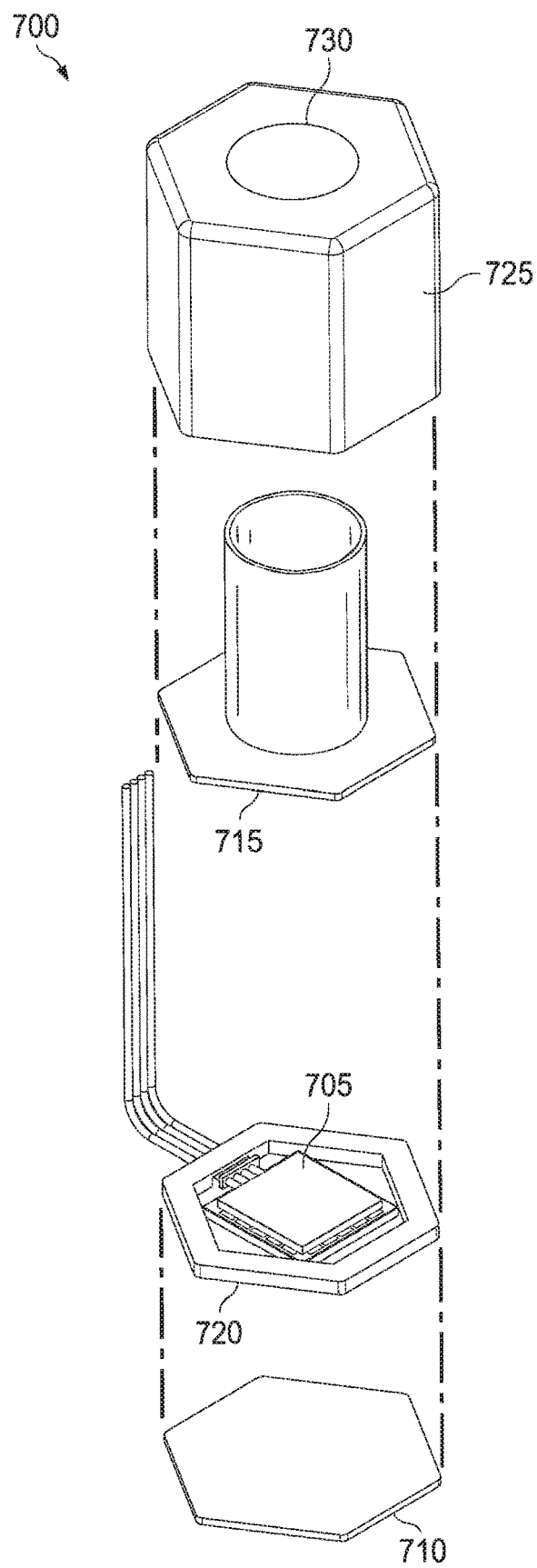
FIG. 7 illustrates an exploded view for a thermoelectric node according to embodiments of the present disclosure.

FIG. 7 illustrates an exploded view for a thermoelectric node 700 according to embodiments of the present disclosure. The embodiment shown in FIG. 7 is for illustration only. Other embodiments could be used without departing from the scope of the present disclosure.

The thermoelectric node 700 can be one of the thermoelectric nodes 605. The thermoelectric node 700 can include a thermoelectric module 705, a contact spreader 710, a thermal sink 715 with extended surfaces, a structural insulator 720, and an ice reservoir 725.

The thermoelectric module 705 is attached to the circuitry, such as circuitry 615. The circuitry provides directional flow of electricity based on a heating function or cooling function selected by a user. A flow of electricity in a first direction can provide a cooling function on a first surface of the thermoelectric module 705 and a heating function on a second surface of the thermoelectric module 705. Reversing the flow of electricity can provide the heating function on the first surface of the thermoelectric module 705 and the cooling function on the second surface of the thermoelectric module 705. For example, the thermoelectric module 705 can be powered by a DC electrical supply or converter that has an output equal to or less than 48 volts.

The contact spreader 710 is connected to the first side or the supply side of the thermoelectric module 705. The contact spreader 710 can be made of a thermally conductive material (for example, aluminum, etc.) to transfer the cold or heat from the thermoelectric module 705 to a surface that the thermoelectric node 700 is treating. It can also be anodized or otherwise coated for corrosion protection. The spreader can also be made of a flexible material. The spreader 710 can also include a contour that allows more contact with the surface area of the specific body part. The spreader 710 can include a corrosion protection coating to protect from moistures, sweat, etc.

The thermal sink 715 is connected to the second side or the waste side of the thermoelectric module 705. The second side is opposite to the first side of the thermoelectric module 705. The thermal sink 715 can be made of a thermally conductive material (for example, aluminum, etc.) to transfer the cold or heat from the waste side of the thermoelectric module to the charged phase change material. It can also include extended surfaces to aid in transferring heat into the PCM. The thermal sink 715 can include a corrosion protection coating to protect from moistures, sweat, etc.

The structural insulator 720 is located around the thermoelectric module 705 between the contact spreader 710 and the thermal sink 715. The structural insulator 720 provides a thermally insulating mechanical structure that removes any excessive forces on the thermoelectric module 705. The structural insulator 720 can be made of insulator materials, such as an insulation foam, that contacts both the contact spreader and the colds sink. The structural insulator 720 can encapsulate the thermoelectric module 705 for protection from outside interference. The structural insulator 720 can interface between the thermal sink 715 and the contact spreader 710 to provide both a mechanical means for coupling and thermal insulation.

The ice reservoir 725 is a cap over the thermal sink 715 and forms a volume for containing a phase change material, for example, water and ice depending on the state. The ice reservoir 725 can be made with a flexible material, such as silicon. A cap 730 located on the ice reservoir 725 can be used to refill the phase change material used. The cap 730 allows the PCM reservoir to be drained or filled.

Figure 8:
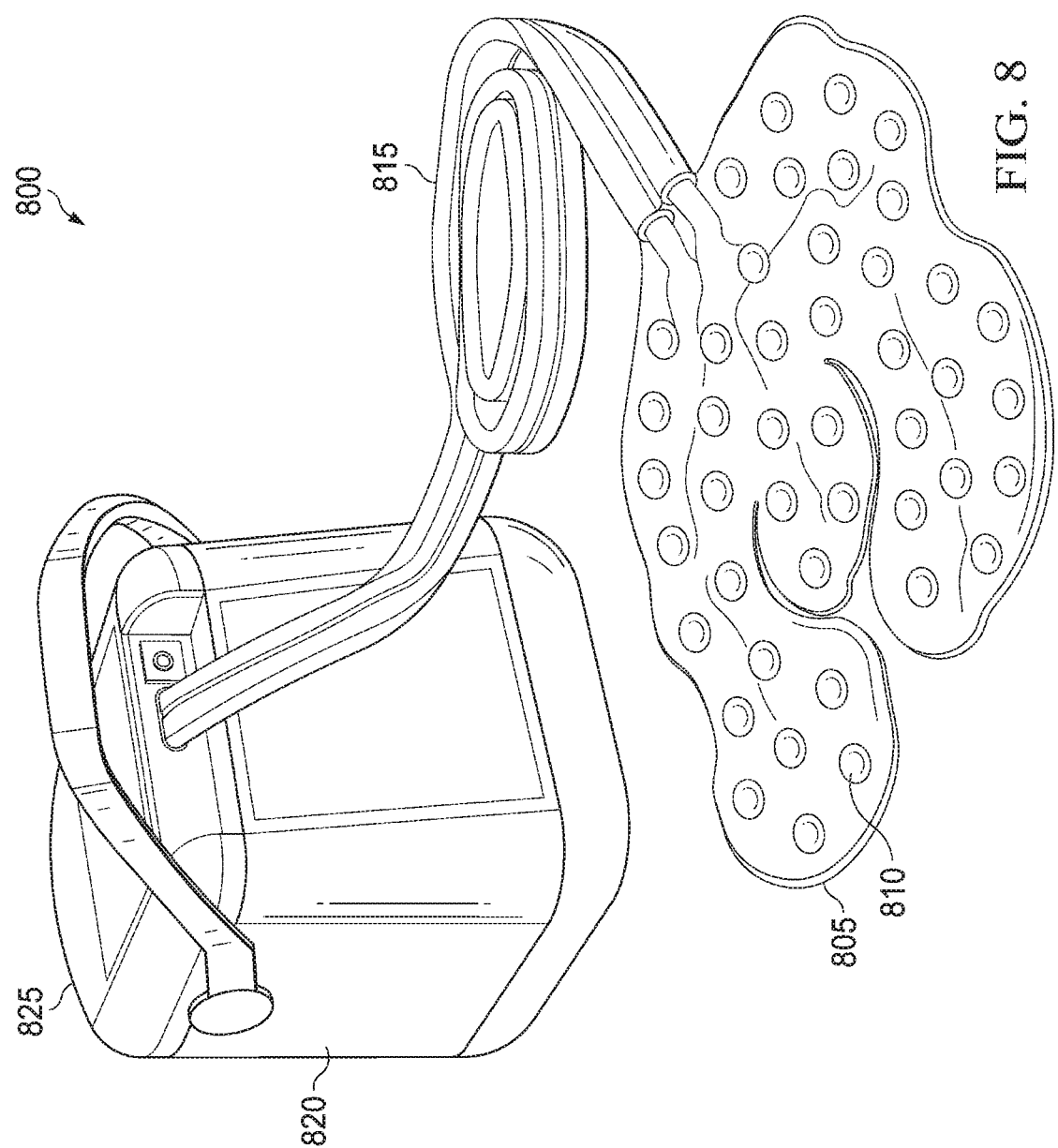
FIG. 8 illustrates a smart chill pad according to embodiments of the present disclosure.

FIG. 8 illustrates a smart chill pad 800 according to embodiments of the present disclosure. The embodiment shown in FIG. 8 is for illustration only. Other embodiments could be used without departing from the scope of the present disclosure.

The smart chill pad 800 includes a pad 805 with a plurality of thermoelectric modules 810 attached, a flow path 815, a PCM reservoir 820 and a pump 825. The flexibility of the smart chill pad 800 can be used on various locations and shapes to provide heating or cooling effects.

The pad 805 is made of a flexible material that has low thermal conductivity outside of the locations of the plurality of thermoelectric modules 810. The locations of the plurality of thermoelectric modules 810 can have a different material for the pad 805 or a thermal sink can be fitted to expose the thermoelectric modules to the phase change material in the flow path 815.

The flow path 815 circulates from the PCM reservoir 820 through the pad 805 contacting a waste side of each thermoelectric module 810. The flow path 815 can be a single path through the pad 805 or multiple paths through the pad 805. The flow path 815 allows for a larger PCM reservoir 820 and also can include connections for switching PCM reservoirs 820 for extend use of the chill pad 800. The PCM reservoir 820 can be provided separately from the pad 805 in a manner that allows an increased amount of heat transfer on the waste side of each of the thermoelectric modules 810.

The pump 825 circulates the chilled liquid from the phase change material reservoir 820 through the flow path 815. The speed of the pump can be adjusted based on use of the pad. When a higher temperature is being operated for each of the TECs, the pump 825 can increase the flow of the liquid. The pump 825 can also be adjusted based on the liquid temperature circulating through the phase change reservoir 820.

Figure 9:
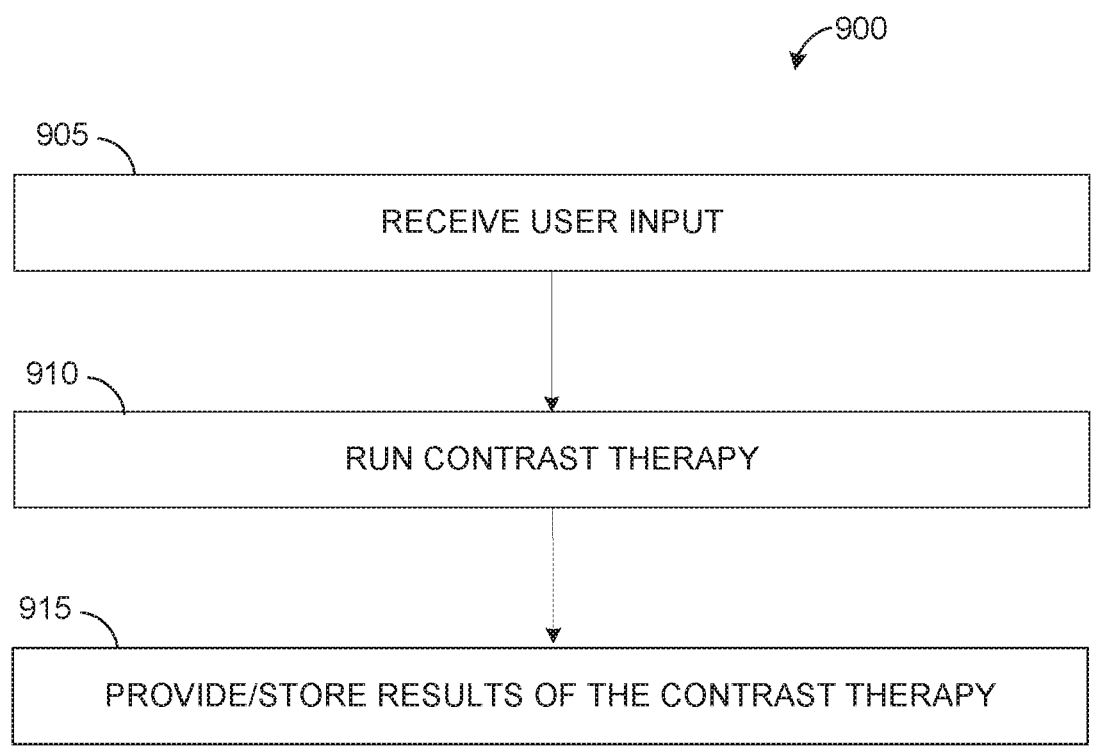
FIG. 9 illustrates a process for a thermoelectric contrast therapy device in accordance with various embodiments of the present disclosure.

FIG. 9 illustrates a process for a thermoelectric contrast therapy device in accordance with various embodiments of the present disclosure. For example, the process depicted in FIG. 9 may be performed by the electronic device 1000 in FIG. 10.

In operation 905, the electronic device 1000 receives a user input. The input could include a timer, a cycle count, a cycle ratio, a hot temperature set point, a cold temperature set point, different region settings, set times for each part of the cycle, transition time between the heating and the cooling, etc. Along with the inputs, the PCM is frozen or pre-charged before use. Inputs accepted can also be limited to those that are safe for user operation.

In operation 910, the electronic device 1000 runs the contrast therapy using the thermoelectric device. The electronic device 1000 controls an electrical energy and direction of the electrical energy to a thermoelectric device based on the received set points and sensor/timer feedback. The electronic device 1000 controls the amount of time or cycles the contrast therapy last. Based on the cycle ratio, the hot and cold temperature set points, and transition times, the electronic device switches between the hot and cold cycles of the contrast therapy.

The electronic device 1000 can control the specific hot and cold temperatures, time of cooling and heating, and number of cycles of the thermoelectric device to avoid tissue damage. The electronic device 1000 monitors the temperature of the contact spreader in an effort for avoiding tissue damage. Fail safe points are pre-set or can be adjusted to protect the user.

A temperature measurement device such as a thermistor can be attached to each side of the thermoelectric device for monitoring the temperatures on the hot side and the cold side. The thermistor on the waste side of the thermoelectric device can monitor a temperature of the ice reservoir to ensure that each thermoelectric node 700 does not thermally run away causing damage to the user or the smart thermoelectric contrast therapy device itself.

In operation 915, the electronic device 1000 can provide or store the results of the contrast therapy. The electronic device 1000 can document the contrast therapy including the temperature set points, the time to completion or performed, a body part that is receiving the therapy, etc.

Although FIG. 9 illustrates an example a process for operating a thermoelectric contrast therapy device, respectively, various changes could be made to FIG. 9. For example, while shown as a series of steps, various steps in each figure could overlap, occur in parallel, occur in a different order, or occur multiple times.

Figure 10:
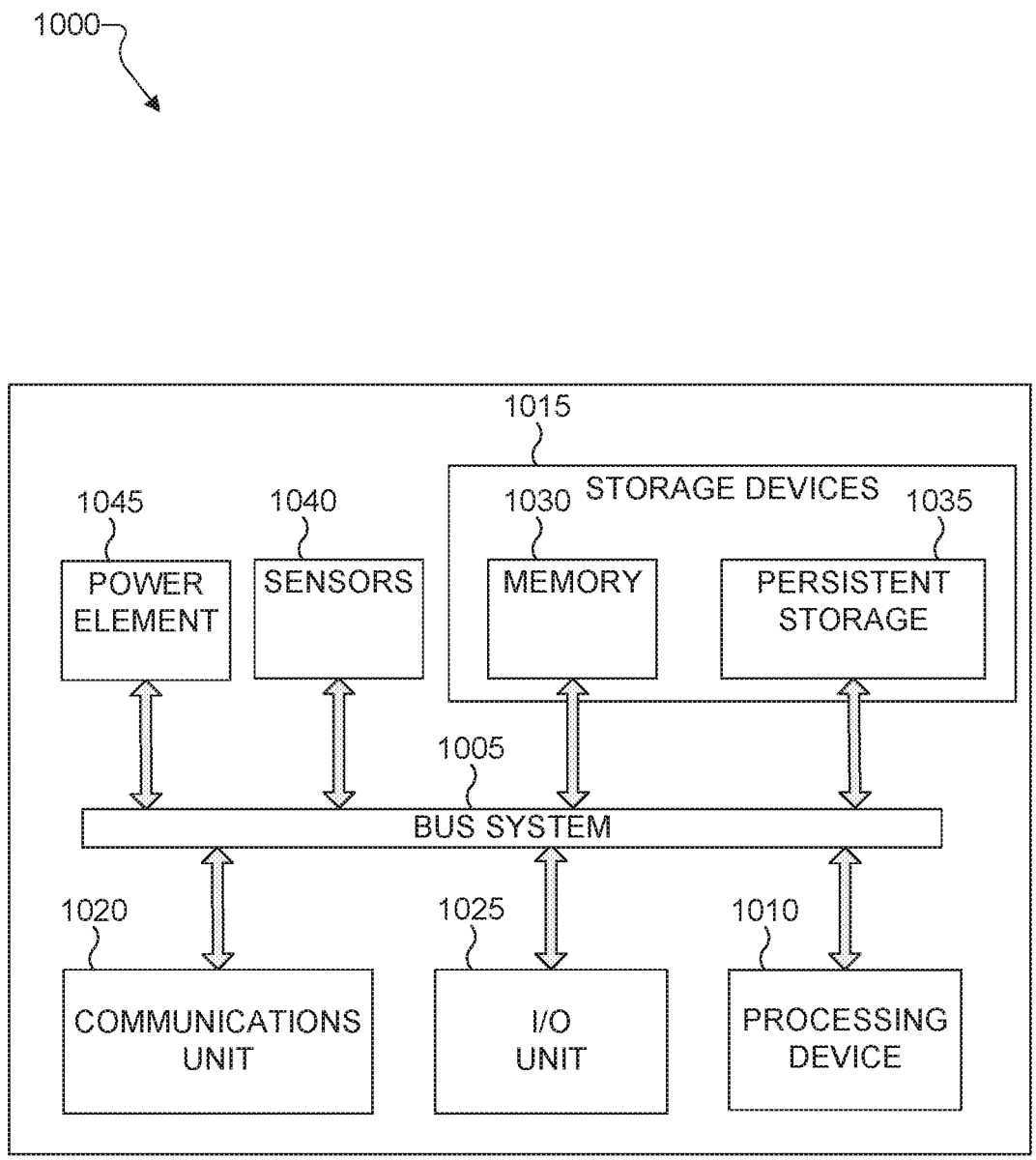
FIG. 10 illustrates an example device implemented with a thermoelectric contrast therapy device according to this disclosure.

FIG. 10 illustrates an example device according to this disclosure. The embodiment shown in FIG. 10 is for illustration only. Other embodiments could be used without departing from the scope of the present disclosure.

As shown in FIG. 10, the electronic device 1000 includes a bus system 1005, which supports communication between at least one processing device 1010, at least one storage device 1015, at least one communications unit 1020, at least one input/output (I/O) unit 1025, at least one sensor 1040, and a power element 1045.

The processing device 1010 executes instructions that may be loaded into a memory 1030. The processing device 1010 may include any suitable number(s) and type(s) of processors or other devices in any suitable arrangement. Example types of processing devices 1010 include microprocessors, microcontrollers, digital signal processors, field programmable gate arrays, application specific integrated circuits, and discreet circuitry. The processing device 1010 can be programmable or can download cycle parameters characteristics of different body parts and treatment cycles. Cycle parameters can include supply side temperatures and times.

The memory 1030 and a persistent storage 1035 are examples of storage devices 1015, which represent any structure(s) capable of storing and facilitating retrieval of information (such as data, program code, and/or other suitable information on a temporary or permanent basis). The memory 1030 may represent a random access memory or any other suitable volatile or non-volatile storage device(s). The persistent storage 1035 may contain one or more components or devices supporting longer-term storage of data, such as a ready only memory, hard drive, flash memory, or optical disc. The persistent storage 1035 includes the instructions for regulating the heating and cooling functions of the thermoelectric contrast therapy device.

The communications unit 1020 supports communications with other systems or devices. For example, the communications unit 1020 could include a network interface card or a wireless transceiver facilitating communications over the network 102. The communications unit 1020 may support communications through any suitable physical or wireless communication link(s). The communications unit 1020 could communicate with a wireless device for control of the smart thermoelectric contrast therapy device 600 or the smart chill pad 800.

The I/O unit 1025 allows for input and output of data. For example, the I/O unit 1025 may provide a connection for user input through a keyboard, mouse, keypad, touchscreen, or other suitable input device. The I/O unit 1025 may also send output to a display, printer, or other suitable output device. A display could present programming and contrast therapy information to a user. The I/O unit 1025 can also include a plurality of LEDs that indicate specific operating statuses, such as heating, cooling, standby, etc.

The sensor 1040 can provide feedback of the contrast therapy to the user or stored in the storage device 1015. Sensors 1040 can include temperature sensors, pressure sensors, biometric sensors, etc.

The power element 1045 provides power to the different components of the electronic device, either directly or through bus 1005. The power element can by an internal battery or a connection for an external power supply.

As described in more detail above, the electronic device 1000 can be internal or external to a thermoelectric contrast therapy device. The electronic device 1000 controls the direction of electricity across the thermoelectric module 105. The electronic device 1000 controls the alternating of the current to provide contrast therapy.

Although FIG. 10 illustrates an example of an electronic device 1000, various changes may be made to FIG. 10. For example, various components in FIG. 10 could be combined, further subdivided, or omitted and additional components could be added according to particular needs. As a particular example, the processing device 1010 could be divided into multiple processors, such as one or more central processing units (CPUs) and one or more graphics processing units (GPUs). In addition, as with computing and communication networks, electronic devices can come in a wide variety of configurations, and FIG. 10 does not limit this disclosure to any particular electronic device.

Figure 11:
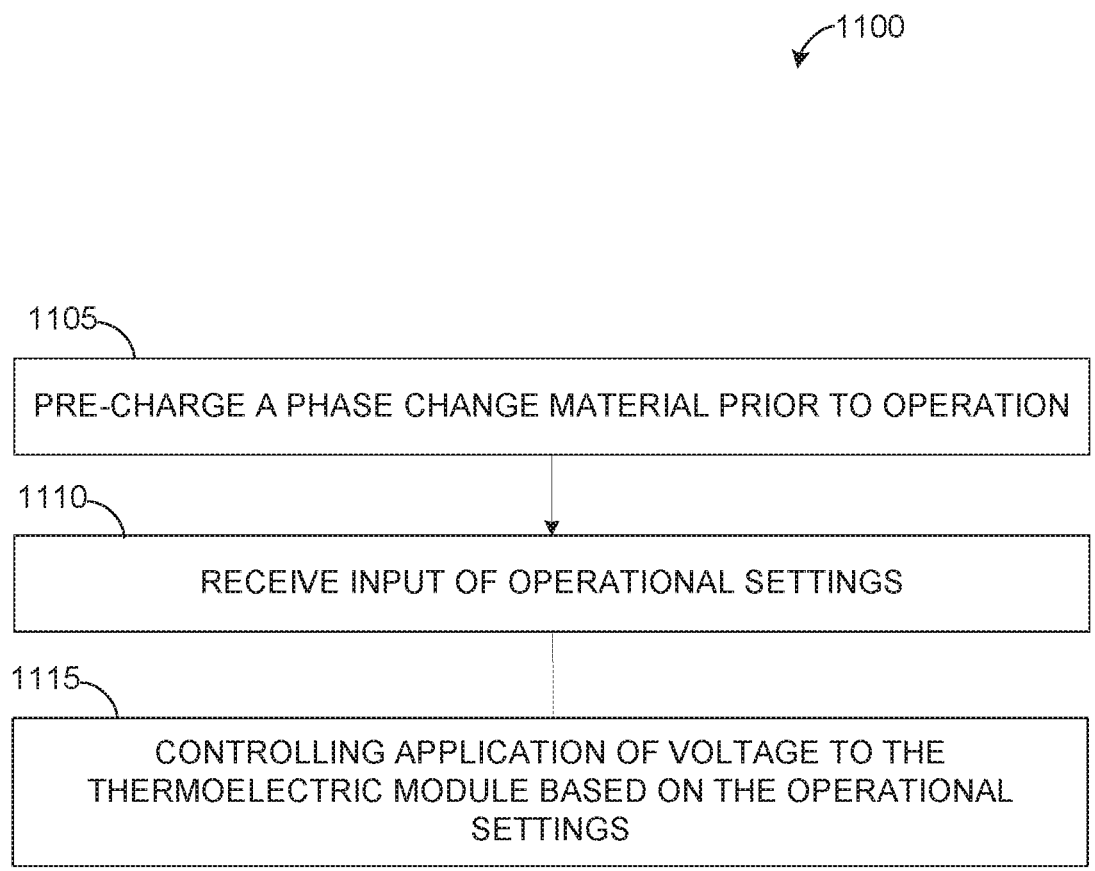
FIG. 11 illustrates a process for applying contrast therapy to a body using a thermoelectric contrast therapy device in accordance with various embodiments of the present disclosure.

FIG. 11 illustrates a process 1100 for applying contrast therapy to a body using a thermoelectric contrast therapy device in accordance with various embodiments of the present disclosure. For example, the process depicted in FIG. 11 may be performed by the electronic device 1000 in FIG. 10.

In operation 1105, the PCM can be pre-charged prior to using in the contrast therapy. The PCM can be frozen in advance of use. The PCM is used to increase the efficiency of the thermoelectric module by increasing the disbursement of heat waste during the cooling operations.

In certain embodiments, the PCM can be filled or refilled in the reservoir as suitable for the contrast therapy. The PCM reservoirs themselves can be interchangeable for extended contrast therapy.

In operation 1110, the electronic device 1000 can receive input of operational settings of the thermoelectric module. "Receiving" the input of operational settings can include loading the operational settings from memory, having a user input the operational settings directly to the electronic device 1000 or the thermoelectric contrast therapy device, or receiving wireless signals including the operational settings from an external device.

Either before or after operation 1110, the thermoelectric contrast therapy device can be inserted into a strap designed for a specific body part. Examples of specific body parts can include wrist, elbows, forearms, foot, heel, shin, knee, etc. The strap can be attached to the specific body part.

In certain embodiments, the thermoelectric contrast therapy device can have the internal power storage changed or be plugged in to a wall.

The thermoelectric contrast therapy device can also include connections for interconnecting multiple thermoelectric contrast therapy devices. The connections can include magnets, physical connections, etc.

In operation 1115, the electronic device 1000 can control an application of an input voltage applied to a thermoelectric device based on the received operational set points, wherein the application includes an amount of the input voltage and a polarity of the input voltage. The polarity of the input voltage controls whether the heating function or the cooling function is applied at the supply side of the thermoelectric contrast therapy device. The amount of the input voltage controls the intensity or degree of the heating and cooling functions on the supply side of the thermoelectric contrast therapy device.

In certain embodiments, the electronic device 1000 can receive signals from an external device for controlling the thermoelectric module. The external device can transmit a signal including an amount and a polarity of the input voltage. The electronic device 1000 can upload usage history data of the application of the input voltage for the thermoelectric device. The usage history data can be uploaded to the external device or to a cloud account. The usage history data can be transmitted includes the amount and polarity of the input voltage, the measured temperatures on the supply side and the waste side of the thermoelectric module, measured temperatures of the reservoir, etc.

Although FIG. 11 illustrates an example a process for applying contrast therapy to a body using a thermoelectric contrast therapy device, respectively, various changes could be made to FIG. 11. For example, while shown as a series of steps, various steps in each figure could overlap, occur in parallel, occur in a different order, or occur multiple times.

Although the present disclosure has been described with exemplary embodiments, various changes and modifications may be suggested to one skilled in the art. It is intended that the present disclosure encompass such changes and modifications as fall within the scope of the appended claims.

One embodiment provides a method for applying contrast therapy to a body using a thermoelectric contrast therapy device. The method includes pre-charging a phase change material (PCM) contained in a reservoir, wherein the PCM contacts a thermal sink on a waste side of a thermoelectric module; providing opposite heating and cooling functions using a supply side and the waste side of the thermoelectric module based on a polarity of an input voltage applied to the thermoelectric module, wherein a spreader is positioned on the supply side of the thermoelectric module and the thermal sink contacts the waste side of the thermoelectric module; and directing, using a controller, the heating and cooling functions as well as timing functions.

Another embodiment provides thermoelectric contrast therapy node. The thermoelectric contrast therapy node includes a thermoelectric module, a phase change material (PCM), a reservoir, a thermal sink, a spreader, and a controller. The thermoelectric module structured with a supply side and a waste side, where the supply side and the waste side provide opposite heating and cooling functions based on a polarity of an input voltage applied to the thermoelectric module. The phase change material (PCM) positioned on the waste side of the thermoelectric module, wherein the PCM is capable of being pre-cooled before operation of the thermoelectric module. The reservoir configured to contain the PCM. The thermal sink that contacts the PCM and the thermoelectric module. The spreader positioned on the supply side of the thermoelectric module. The controller configured to direct the heating and cooling functions as well as timing functions.

Another embodiment provides a thermoelectric contrast therapy device. The thermoelectric contrast therapy device includes a control node and a plurality of thermoelectric nodes. The control node is electrically and mechanically connected to a plurality of thermoelectric nodes, the control node configured to direct the heating and cooling functions as well as timing functions. Each of the plurality of thermoelectric nodes includes a thermoelectric module, a phase change material (PCM), a reservoir, a thermal sink, a spreader, and a controller. The thermoelectric module structured with a supply side and a waste side, where the supply side and the waste side provide opposite heating and cooling functions based on a polarity of an input voltage applied to the thermoelectric module. The phase change material (PCM) positioned on the waste side of the thermoelectric module, wherein the PCM is capable of being pre-cooled before operation of the thermoelectric module. The reservoir configured to contain the PCM. The thermal sink that contacts the PCM and the thermoelectric module. The spreader positioned on the supply side of the thermoelectric module. The controller configured to direct the heating and cooling functions as well as timing functions.

In any of the above examples and embodiments, receiving operational set points for an operation of the supply side of the thermoelectric module, wherein the operational set points include hot parameters, cold parameters and timing parameters; and controlling an application of the input voltage applied to a thermoelectric device based on the received operational set points, wherein the application includes an amount of the input voltage and the polarity of the input voltage may be included.

In any of the above examples and embodiments, controlling the thermoelectric module using wireless communication circuitry to communicate with an external device; and uploading usage history data of the application of the input voltage for the thermoelectric module may be included.

In any of the above examples and embodiments, inserting the thermoelectric contrast therapy device in a strap designed for a specific body part; and attaching the strap to the specific body part may be included.

In any of the above examples and embodiments, the thermal sink extends into the PCM for enhanced heat transfer may be included.

In any of the above examples and embodiments, a supply temperature sensor located on the supply side of the thermoelectric module; and a waste temperature sensor located on the waste side of the thermoelectric module may be included.

In any of the above examples and embodiments, structural foam provided between the thermal sink and the spreader and configured to mechanically couple and thermally isolated the thermal sink and the spreader may be included.

In any of the above examples and embodiments, the thermoelectric module is electrically isolated from the thermal sink and the spreader may be included.

In any of the above examples and embodiments, a reservoir to contain the PCM for each of the thermoelectric nodes may be included.

In any of the above examples and embodiments, each of the thermoelectric nodes further comprises a reservoir to contain the PCM may be included.

In any of the above examples and embodiments, an external reservoir containing the PCM; a PCM loop connecting the external reservoir to each of the thermal sinks; and a pump configured to circulate the PCM through the PCM loop may be included.

In any of the above examples and embodiments, connections to attach at least one of the thermoelectric nodes to at least one thermoelectric nodes of a second thermoelectric contrast therapy device may be included.

In any of the above examples and embodiments, the control node is further configured to provide different amounts of input power and the polarity of the input voltage to individual thermoelectric nodes may be included.

None of the description in this application should be read as implying that any particular element, step, or function is an essential element that must be included in the claim scope. The scope of the patented subject matter is defined only by the claims. Moreover, none of the claims is intended to invoke 35 U.S.C. § 112(f) unless the exact words "means for" are followed by a participle.

What is claimed is:

1. A method for applying contrast therapy to a body using a thermoelectric contrast therapy device, the method comprising:
    pre-charging a phase change material (PCM) into a flexible reservoir, wherein the PCM contacts a thermal sink on a waste side of a thermoelectric module;
    freezing the PCM;

providing opposite heating and cooling functions using a supply side and the waste side of the thermoelectric module based on a polarity of an input voltage applied to the thermoelectric module, wherein a spreader is positioned on the supply side of the thermoelectric module and the thermal sink contacts the waste side of the thermoelectric module, wherein the thermal sink is elongated, includes a plurality of surfaces, and extends into the PCM such that the PCM surrounds the plurality of surfaces;

cooling the spreader by transferring heat from the spreader to the PCM, following the cooling, heating the spreader by transferring heat from the PCM to spreader, following the heating, cooling the spreader by transferring heat from the spreader to the PCM; and;

directing, using a controller, the heating and cooling functions as well as timing functions.

2. The method of claim 1, further comprising:
receiving operational set points for an operation of the supply side of the thermoelectric module, wherein the operational set points include hot parameters, cold parameters and timing parameters; and
controlling an application of the input voltage applied to a thermoelectric device based on the received operational set points, wherein the application includes an amount of the input voltage and the polarity of the input voltage.

3. The method of claim 2, further comprising:
controlling the thermoelectric module using wireless communication circuitry to communicate with an external device; and
uploading usage history data of the application of the input voltage for the thermoelectric module.

4. The method of claim 1, further comprising:
inserting the thermoelectric contrast therapy device in a strap designed for a specific body part; and
attaching the strap to the specific body part.

5. A thermoelectric contrast therapy node comprising:
a thermoelectric module structured with a supply side and a waste side, wherein the supply side and the waste side provide opposite heating and cooling functions based on a polarity of an input voltage applied to the thermoelectric module;
a phase change material (PCM) positioned on the waste side of the thermoelectric module, wherein the PCM is frozen;
a flexible reservoir containing the PCM;
a thermal sink that contacts the PCM and the thermoelectric module, wherein the thermal sink is elongated, includes a plurality of surfaces, and extends into the PCM such that PCM surrounds the plurality of surfaces for enhanced heat transfer;
a spreader positioned on the supply side of the thermoelectric module;
an insulator disposed between the thermal sink and the spreader and configured to mechanically couple and thermally isolated the thermal sink and the spreader; and
a controller configured to direct the heating and cooling functions as well as timing functions.

6. The thermoelectric contrast therapy node of claim 5, further comprising:
a supply temperature sensor located on the supply side of the thermoelectric module; and
a waste temperature sensor located on the waste side of the thermoelectric module.

7. The thermoelectric contrast therapy node of claim 5, wherein the insulator comprises structural foam provided between the thermal sink and the spreader.

8. The thermoelectric contrast therapy node of claim 5, wherein the thermoelectric module is electrically isolated from the thermal sink and the spreader.

9. A thermoelectric contrast therapy device comprising:
a plurality of the thermoelectric node according to claim 5; and
a control node electrically and mechanically connected to the plurality of thermoelectric nodes, the control node configured to direct the heating and cooling functions as well as the timing functions of the controller for the plurality of thermoelectric nodes.

10. The thermoelectric contrast therapy device of claim 9, further comprising:
an external reservoir containing the PCM;
a PCM loop connecting the external reservoir to each of the thermal sinks; and
a pump configured to circulate the PCM through the PCM loop.

11. The thermoelectric contrast therapy device of claim 10, further comprising connections to attach at least one of the thermoelectric nodes to at least one thermoelectric nodes of a second thermoelectric contrast therapy device.

12. The thermoelectric contrast therapy device of claim 9, wherein the control node is further configured to provide different amounts of input power and the polarity of the input voltage to individual thermoelectric nodes.

13. A device to provide thermoelectric contrast therapy to a surface using input voltage and a phase change material (PCM), the device comprising:
a flexible pad;
a controller configured to direct the input voltage and configured to control a polarity thereof; and
a plurality of thermoelectric nodes disposed on the flexible pad and being conformable therewith to the surface, each of the thermoelectric nodes comprising:
a thermoelectric module in electrical communication with the controller and having a supply side and a waste side, the supply and waste sides being configured to provide opposite heating and cooling functions based on the polarity of the input voltage directed to the thermoelectric module;
a node reservoir containing the PCM, wherein the PCM is frozen and the node reservoir is flexible;
a thermal sink disposed on the waste side of the thermoelectric module, wherein the thermal sink is elongates, includes a plurality of surfaces, and extends into the PCM contained in the node reservoir such that the PCM surrounds the plurality of surfaces;
a spreader disposed on the supply side of the thermoelectric module; and
an insulator disposed between the thermal sink and the spreader and configured to mechanically couple and thermally isolated the thermal sink and the spreader.

14. The device of claim 13, further comprising at least one circuitry node electrically and mechanically connected to the plurality of thermoelectric nodes and directing the electrical communication of the thermoelectric modules with the controller.

15. The device of claim 13, further comprising:
an external reservoir containing the PCM;
a PCM loop connecting the external reservoir to each of the node reservoirs; and a pump configured to circulate the PCM through the PCM loop.

\* \* \* \* \*